United States Patent
Svadovskiy

(10) Patent No.: US 6,936,049 B2
(45) Date of Patent: Aug. 30, 2005

(54) METHOD OF NEUROSURGICAL TREATMENT OF INFANTILE CEREBRAL PALSY

(76) Inventor: Aleksandr Igorevich Svadovskiy, kv. 24, Korp.2.D.4, UL. Bolshaya Cherkizovskaya, Moscow 105187 (RU)

( * ) Notice: Subject to any disclaimer, the term of this patent is extended or adjusted under 35 U.S.C. 154(b) by 669 days.

(21) Appl. No.: 10/134,331

(22) Filed: Apr. 29, 2002

(65) Prior Publication Data

US 2003/0014055 A1 Jan. 16, 2003

(30) Foreign Application Priority Data

Jul. 12, 2001 (RU) ............................ 2001119205

(51) Int. Cl.$^7$ ............................................. A61B 17/58
(52) U.S. Cl. ............................................. 606/61; 606/86
(58) Field of Search ............................ 606/61, 53, 79, 606/86

(56) References Cited

U.S. PATENT DOCUMENTS 4,379,462 A * 4/1983 Borkan et al. .............. 607/117
5,002,053 A * 3/1991 Garcia-Rill et al. .......... 607/49
5,255,691 A * 10/1993 Otten ......................... 607/117

* cited by examiner

Primary Examiner—David O. Reip
(74) Attorney, Agent, or Firm—J. Herbert O'Toole; Nexsen Pruet, LLC

(57) ABSTRACT

A method of neurosurgical treatment of infantile cerebral palsy wherein laminectomy is performed for providing access to the vertebral canal and its contents. The laminectomy is carried out in the cervical portion of the spine and the removal of at least three vertebral arches is effected.

5 Claims, No Drawings

METHOD OF NEUROSURGICAL TREATMENT OF INFANTILE CEREBRAL PALSY

FIELD OF THE ART

The present invention relates to medicine, and more particularly to a method of neurosurgical treatment of infantile cerebral palsy.

The present invention may be used in surgery, and more exactly in neurosurgery.

DESCRIPTION OF PRIOR ART

It is known that the notion "infantile cerebral palsy" (ICP) includes an organic antenatal, perinatal or early neonatal injury of the brain with mental, psychic and motor retardation of the child. ICP is a polyetiologic disease: pathological factors leading to ICP development may be: various infections transmitted from the mother to the fetus during pregnancy, a birth injury, ischemic and hypoxic disturbances in the central nervous system (for instance, infantile asphyxia). Sometimes the disease commences at the pre-school or school age, and even in adolescence, against the background of an illness, psychoemotional overstrain or vaccination one has come through. One of the most severe, invalidizing manifestations of ICP are motor disorders, spastic hemi- or tetraparesis or tetraplegia. It is believed a priori that these motor disturbances depend on the extent of cerebral injury. Dysfunctions of pelvic organs of the enuresis type are also often observed in ICP. In computer tomography and magnetic resonance tomography images, as a rule, features of focal lesion(s) of the brain substance are revealed, predominantly in the white substance of cerebral hemispheres, with the formation of cysts and/or focal degeneration (degradation).

Numerous conservative methods of ICP treatment are known, comprising medicamentous therapy aimed at improving metabolism in the brain, massage, physiotherapy, remedial gymnastics, general health-improving therapy, kinesitherapy, as well as surgical and neurosurgical methods of treating comprising orthopedic operations on tendons of extremities, transplantation of embryonic tissue into the brain.

However, the results of such treatment today cannot be regarded as being satisfactory, since any essential regress of dyskinesia or clear-cut positive dynamics in the aspects of mental development, psychic functions, and the functions of pelvic organs are absent. The above-cited approaches to the treatment of ICP proceed exclusively from cerebral affection only and the ensuing motor, psychic, intellectual deficit, dysfunction of pelvic organs, as well as other disorders.

Known in the art is a method of neurosurgical treatment in the case of ICP (spastic diplegia, hemiplegia, tetraplegia): selective posterior rhizotomy or surgical section of the posterior spinal nerve roots. The operation is performed in the lumbar section of the spine. However, said operation (surgical section of the motor roots) in essence is an invalidizing operation and does not lead to an actual reduction of spasticity, improvement in the motor functions and other positive changes (S. V. Gaskill and A. E. Merlin in "Handbook of Pediatric Neurology and Neurosurgery" (Russian translation, 1996, Moscow)).

When this kind of neurosurgical intervention is performed on the cervical section, 50% of the patients develop serious respiratory complications which require resuscitation measures, the treatment this becoming more complicated.

A method of the neurosurgical treatment of infantile cerebral palsy is known, namely, a method of selective dorsal rhizotomy for treating spasticity in patients suffering from infantile cerebral palsy (see "Voprosy Neirokhirurgii", 1966, No. 3, pp. 19–22, I. N. Shevelev et al., "Applying Selective Dorsal Rhizotomy Cut Spinal Roots for Treating Spasticity in Patients Suffering from Infantile Cerebral Palsy"), which involves performing laminectomy for access to the vertebral canal and its contents (the motor roots). The laminectomy is performed on the lumbar level, and the operation is limited to the removal of one or two vertebral arches. When treating with this method, it is difficult to identify completely all the fibers responsible for the motor functions of a patient. Due to the presence of multiple motor disorders in a patient, it is necessary to perform the operation on several motor roots, both from the right and from the left, and also on several levels, which may require several surgical interventions. This complicates considerably restoration of lost neurologic functions and rehabilitation. With this method of treatment, it is possible to achieve only a partial, uncontrollable alleviation of spasticity in patients suffering from infantile cerebral palsy. On performance of a posterior selective rhizotomy operation, spastic palsy of the upper and lower extremities is not eliminated at once and completely, truncal cerebral disorders, i.e., dysarthria, aphonia, hypersalivation, and other symptoms are not eliminated either. This method does not insure elimination of hidden in obvious compression of the roots of the spinal cord and of the truncus cerebri. Hence, the psychic state and intellectual abilities of patients do not become improved, and, ultimately, the effectiveness of the treatment is not high. Furthermore, this method is not physiological, since it involves anatomic interruption of the natural conduction motor tracts in a patient.

DISCLOSURE OF THE INVENTION

The present invention is directed to the provision of a method of neurosurgical treatment of infantile cerebral palsy, wherein, owing to performing standard laminectomy in a prescribed portion of the spine, elimination of hidden in obvious compression of the roots of the very spinal cord and of the truncus cerebri is provided, thereby eliminating the present status of spastic paresis or palsy of the upper and lower extremities, truncal cerebral disorders, and improving the psychic condition and intellectual abilities of patients, this, in the final count, making it possible to increase the effectiveness of treatment.

The set object is accomplished by a method of neurosurgical treatment of infantile cerebral palsy, which consists in performing laminectomy for access to the vertebral canal and its contents. According to the invention, laminectomy is performed in the cervical portion of the spine, and the removal of at least three vertebral arches is carried out.

Prior to the laminectomy an additional examination may be carried out.

An additional examination may comprise ultrasonic transcranial dopplerography with investigating the cerebral blood flow rate and the Gosling pulse index along vertebral arteries, and computer thermal imaging investigation of the posterior surface of the neck.

After the removal of vertebral arches, in the case of multiple small tears of the dura mater with liquorrhea, it is expedient to apply at least one bioprotector strip to the dura mater.

It is also expedient after the removal of vertebral arches to install a posterior spondylodesis from a material biocompatible with the patient's organism in the area of the laminectomy window.

The present invention makes it possible to raise the effectiveness of treatment, to simplify and cheapen the treatment, to obviate prolonged hospitalization of patients, to rule out various consequences associated with invalidizing operations, and it does not involve complications. The proposed method also makes it possible not only to improve motor functions but to completely eliminate the status of the spastic palsy of upper and lower extremities. The present invention improves the psychic condition and intellectual abilities of the patient, eliminates truncal cerebral disorders, such as dysarthria, aphonia, hypersalivation, and other symptoms. In ICP patients after examination the fact is objectively established that along with an organic injury of the brain there is an in obvious, hardly identifiable (by a number of indirect features) injury of the cervical part of the spine, compression of the spinal cord and its roots on this level. It is obvious that lost motor and other functions cannot be restored without elimination of this compression. The present method of nation of this compression. The present method of treatment enables the elimination of said compression of the roots of the very spinal cord and of the brain trunk.

The invention will further be explained by examples of its embodiments.

The present method of treating infantile cerebral palsy consists in performing laminectomy for access to [performing laminectomy for access to] the vertebral canal and its contents (the spinal cord, motor roots, dura mater). Before the laminectomy, if the necessary technical equipment is available, ICP patients are thoroughly examined, and as a result the fact is objectively established that along with an organic injury of the brain there is an in obvious, hardly identifiable (by a number of indirect features) injury of the cervical part of the spine, compression of the spinal cord and its roots on this level. It is obvious that lost motor and other functions cannot be restored without elimination of this compression, said additional examination comprises ultrasonic transcranial dopplerography with investigating the cerebral blood flow rate and the Gosling pulse index along vertebral arteries and computer thermal imaging investigation of the posterior surface of the neck. Laminectomy is performed without opening the dura mater, without any approach to the place of outgoing of the roots from the vertebral canal and manipulations thereon, i.e., no intervention on the spinal cord proper is required. Laminectomy is performed under general anesthetic. A linear incision is made in the projection of cervical vertebrae, extending from the external occipital tuber to the seventh cervical vertebra. Then spinous processes are freed from paravertebral muscles, the spinous processes are removed in the mid-cervical portion, in the beginning of the second-third-fourth cervical vertebrae, with subsequent removal of the arches of these vertebrae. The scope of the laminectomy, i.e., its extension, is determined during the operation, i.e., decided individually in each particular case, proceeding from the propagation of epiduritis (cicatricialcomissural process of the cellular tissue located atop the dura mater). Injury of this cellular tissue leads to polyradiculomyeloischemia, including the trunk of the brain, and brings about clinical status development. The upper (the first cervical vertebra) and the lower (the fifth, sixth and seventh cervical vertebrae) portions of the posterior half-ring are cracked, if clinically necessary. In such a case, as a rule, there is revealed a status of an expressed epiduritis, distinct thinness of the adjacent dura mater, its adhesion in separate places with the right and left vertebral arches to be removed, small multiple tears of the dura mater, and liquorrhea. In some cases of follow-up after the performed laminectomy, through said multiple tears of the dura mater a gradual change in the color of the dorsal surface of the spinal cord from white or pale pink to dark red is determined intraoperatively. Such intraoperative dynamic change in the color of the spinal cord is connected with development of post-ischemic hyperfusion of the spinal cord, this being indicative that compression of the cervical portion of the spinal cord had been present before the laminectomy was performed. On completion of the neurosurgical intervention, suturing of the multiple small tears of the dura mater is not carried out. For stopping liquorrhea from such tears in the dura mater, at least one strip of a biological protector is placed topically onto the dura mater. As the biological protector use may be made of a commonly known hemostatic sponge (see "NEUROSURGERY", June 1996, vol. 38, No. 6, Williams and Wilkins, pp. 6–15) or of toxocomb (see "Brain Injury", Proceedings of the 5th International Symposium, St. Petersburg, 1999, p. 486 (in Russian)). The number of strips to be placed depends on the intensity of the liquorrhea. On completion of the neurosurgical intervention, it is also possible to install a posterior spondylodesis from a material biocompatible with the patient's organism in the area of the laminectomy window. This installing is carried out with a view to preventing possible or already established instability in the cervical portion of the spine, which leads to a secondary lesion of the spinal cord. The spondylodesis is made from titanium, since it is most biologically inert and compatible with tissues of the patient's organism (see "NEUROSURGERY", June 1996, vol. 38, No. 6, Williams and Wilkins, pp. 17–18).

The development of epiduritis (inflammation of the epidural cellular tissue) plays a role in the pathogenesis of the development of spastic palsy of upper and lower extremities. The role of the epidural venous system in the collateral blood circulation in the brain and spinal cord cavity has been proved (see "Brain Injury", Proceedings of the 5th International Symposium, St. Petersburg, 1999, p. 168, I. I. Tsuladze, "Pathogenesis and Diagnostics of Venous Myelopathologies" (in Russian)). So, upon disturbance of blood circulation in the epidural space, venous outflow from the cranial space into the epidural space is disturbed, and this leads to damage of the brain trunk and of the upper and middle parts of the cervical portion of the spinal cord. Consequently, carrying out laminectomy in the cervical portion in accordance with the present method of neurosurgical treatment leads to removal of the hidden in obvious compression of the roots of the very spinal cord and of the truncus cerebri, thereby eliminating the existent status of spastic palsy of the upper and lower extremities, truncal disorders of the brain, and improving the psychic and intellectual abilities of patients. These, in the final count, making it possible to enhance the effectiveness of treatment.

The herein-proposed method of neurosurgical treatment of infantile cerebral palsy was carried out under clinical conditions. Clinical tests were carried in the neurologic and neurosurgical clinic "Neiroeskulap". The method was used for treating patients afflicted with infantile cerebral palsy, particularly those with spastic or tetra- or hemi-syndrome, retardation of intellectual and psychic development and dysfunctions of pelvic organs.

The proposed method of neurosurgical treatment of infantile cerebral palsy will now be illustrated by examples that follow.

EXAMPLE 1

Female patient A. Aged 9. Diagnosis: ICP, spastic form, deep tetraparesis with predominant lesion of the lower extremities, dysfunction of the pelvic organs of the enuresis type, mental, psychic and motor retardation. From the anamnesis: Mother—first labor, the only child. Father—abused alcoholic drinks. Mother underwent operative intervention in connection with "cleft upper lip".

The girl was born prematurely (6.5 months) in asphyxia. The diagnosis made in the maternity hospital was ICP.

During examination: The girl herself does not present complaints. Her vocabulary of words is sharply limited; the most frequent answer to questions is "don't know". The girl is whiny, and profuse salivation is noted. The patient is in a wheelchair. The posture is with adduction of the arms to the body, contractions with limitation of movements in the fingers and in the wrist joints (flexio). Spontaneous movements in the upper extremities are considerably limited and are possible, mainly, owing to the shoulder joints and, to a smaller extent, to the elbow joints.

Spontaneous movements in the lower extremities are practically absent. The legs are bent (flexio) in the hip joints, knee joints and ankle joints. The overall posture of the patient resembles the so-called "embryonic posture". Atrophy of all the extremities.

The tonus of all the extremities is increased spastically. The presence of sensitivity disorders because of difficulties in speech contact and emotional negative reaction of the child may be checked only conditionally: presumably—hypesthesia from the level of the first, second vertebrae.

The voice is dysphonic, and dysarthria, intermittent coughing when swallowing liquid food, and profuse salivation are present. Paresis of the soft palate, the uvula is deflected to the left.

Ophthalmologist's consultation: the disks of the optic nerves are pale, their boundaries are indistinct, blurred. Partial atrophy of the optic nerves from two sides. The acuity of vision is 0.5–0.6 per eye without correction. Divergent squint.

Magnetic resonance tomography of the brain and of the spinal cord on the cervical level: several large foci of organic lesion of the white substance of the large cerebral hemispheres are revealed in the form of liquid-filled cavities having a magnetic resonance signal similar with the intensity of a liquor signal. The ventricular system is moderately broadened symmetrically, periventricular edema is not determined. Subarachnoidal convexital fissures are sharply broadened. Parachiasmal, cerebellopontal and other cisterns are broadened. The spinal cord in the cervical portion is not changed, the subarachinoidal space is passable.

Ultrasonic transcranial dopplerography of the main extra- and intracranial vessels. Asymmetry of the cerebral blood flow rate along a. vertebrates is determined: 20 cm/s from the right and 40 cm/s from the left. That is, there are symptoms of blood circulation disturbance in the vertebrobasillar system of the brain.

Lumbar puncture. Liquor pressure (LP) is normal. LP=100 mm $H_2O$. The liquor is pure, transparent, and the general analysis is normal. No data on complete or partial blocking of the subarachinoidal space were obtained when carrying out liquorodynamic Queckenstedt's and Stookey's tests. Hence, there is no clear-cut clinical situation indicative of compression of the brain and/or spinal cord. Nevertheless, according to the neurologic data (coarse spastic tetrasyndrome, truncal symptomatics) and to the ultrasonic transcranial dopplerography data, topically the level of lesion could not be accounted for by the organic lesion of the brain only.

Surgery was performed with laminectomy of the second, third, fourth, fifth and sixth cervical vertebrae ($C_2$–$C_6$). It was noted that the dura mater was commissured with the inner surface of the vertebral arches, the epidural cellular tissue was represented by small fragments, thinned, cicatricially modified. On completion of the laminectomy window formation, multiple small tears of the dura mater and liquorrhea from them were seen. 10–15 minutes after the completion of the laminectomy window formation, through the multiple tears of the dura mater a change in the color of the dorsal surface of the spinal cord from white to cyanotic red became visible. The latter phenomenon was interpreted as the development of postischemic hyperfusion of the spinal cord. Plates of hemostatic sponge were placed on the dura mater for tightening the subarachinoidal space.

"Storey-by storey" sutures and Schanz' bandages were placed on the wound.

During the postoperative period, already after the first 24 hours, an improvement in the motor and sensory neurologic functions was noted, as well as an improvement in the aspect of truncal structures. During the nearest postoperative period an essential progress was noted in the psychic and mental development of the child, the status of spastic palsy of the upper and lower extremities was eliminated. No complications or side effects were observed. Healing of the wound proceeded normally. When discharged from the hospital unit, the patient was already able to stand unaided, to hold a spoon, her vocabulary broadened markedly, and she could control the functions of the pelvic organs better.

EXAMPLE 2

Female patient K., aged 6, is registered in a psychoneurologic dispensary. Her mother, while pregnant, had come through influenza. The girl understands when spoken to and carries out simple commands. No spontaneous complaints, but when asked, the girl complains of pains in the cervical portion of the spine. Dysarthria. Pronounced horizontal nystagmus, paresis of the upward eye movement. Deep spastic tetraparesis with the atrophy of muscles of the upper and lower extremities. The patient can move with considerable exterior help, partially controls the functions of the pelvic organs, but on the whole dysfunctions of the enuresis type take place. The girl cannot care for herself, though she can perform some prehensile movements with her hands with respect to large objects. The patient was examined in a stationary hospital.

Lumbar puncture: LP=100 mm $H_2O$, the liquor is pure, transparent. No data on complete (or partial) blocking of the subarachinoidal space were obtained when carrying out liquorodynamic Queckenstedt's and Stookey's tests. In computer tomography images symptoms of diffuse atrophic process are noted, with moderately expressed broadening of the ventricular system but without periventricular edema. Broadening of the basal cisterns and subarachinoidal slots along the convex surface of the brain is revealed. The presence of small cystic (three cortical and one subcortical) formations is observed in the cerebral hemispheres, that are not connected with the ventricular system and do not play a mass effect role. In the magnetic resonance tomography of the cervical portion of the spine and of the spinal cord no pathology data are revealed: the subarachinoidal space is completely passable. No osseous compression pathology is revealed. Ultrasonic dopplerography of the vertebral arteries revealed considerable asymmetry of the linear blood flow: 22 cm/s from the right and 14 cm/s from the left with an increase of the Gosling pulse index to 1.15–1.20, respectively.

Computer thermal imaging investigation reveals a pathological zone of low-temperature signal to 32–33° C. in the projection of posterior portions of the cervical region, this being an indirect indication of the presence of a pathological process there. Classical criteria of compression of the spinal cord and of its roots are absent in the patient.

A neurosurgical intervention, $C_2$–$C_5$ laminectomy, was performed. A status of spread epiduritis with multiple small tears of the dura mater and liquorrhea was revealed postoperatively.

The subarachnoidal space was hermetized with a hemostatic sponge. The postoperative period proceeded smoothly, without serious complications. Healing of the wound by first intention took place. During the first postoperative week a positive neurologic symptomatics was noted in the form of a considerable reduction of spasticity in the upper and lower extremities and appearance of more coordinated small movements in them. Two weeks after the operation, the time of control over the urination and the anal sphincter increased. Dysarthria and hypersalivation, as well as oculomotor disorders regressed substantially. The patient began to elementarily look after herself, her understanding of speech addressed to her improved, and the vocabulary broadened.

EXAMPLE 3

Female patient I., aged 11, has been under constant neurologist's follow-up. ICP diagnosis since the age of 3, right-side spastic hemiparesis, moderately pronounced dysfunctions of the pelvic organs: partial enuresis. The patient can walk unaided with difficulty. Incomplete abduction of the eyeballs from two sides, horizontal nystagmus. Dysarthria. The patient can elementarily care for herself owing to sufficiently good range of movements in the left hand. The patient was treated repeatedly in accordance with traditional scheme without any essential effect. The patient was examined in the clinic "Neiroeskulap". Computer tomography of the brain revealed periventricular degradation of the brain substance without any dominant sidedness. Magnetic resonance tomography did not reveal symptoms of compression in the cervical portion of the spinal cord. Computer thermal imaging investigation revealed a low-temperature pathological signal at 33–34° C. in the projection of the posterior cervical region, this being indicative of the presence of a pathological process in this region, i.e., of a hidden, in obvious compression of the roots of the spinal cord and of the very truncus cerebri.

An operation was performed in accordance with the proposed method of neurosurgical treatment: laminectomy in the upper-middle cervical portion of the spine, and removal of the arches of the second, third and fourth cervical vertebrae ($C_2$–$C_4$) was carried out. Epiduritis, thinning of the dura mater with multiple tears, liquorrhea were revealed. The dura mater was hermetized with a hemostatic sponge plate. In the postoperative period, improvements were noted in the motor and sensory neurologic functions, as well as in the truncal structures already in the first 24 hours. Healing of the wound by first intention took place. In the nearest postoperative period an essential progress was noted in the psychic and mental development of the child. In 5 days, a considerable reduction of spastics in the right extremities, an increase of the range of motions therein, were noted. Dysarthria diminished and the functions of the oculomotor nerves (III, IV and VI pairs of cranial nerves) improved. When being discharged from the clinic, the patient was already able to care for herself, using her right hand. The functions of the pelvic organs became restored.

EXAMPLE 4

Female patient O., aged 12.

Diagnosis: ICP since childhood. The patient was treated repeatedly in a stationary hospital in accordance with the classical scheme. In the neurological status: spastic hemisyndrome in the right extremities. The functions of the pelvic organs are disturbed in the form of frequent imperative urges, but on the whole the patient controls them.

The patient is noted for mental retardation. Nevertheless, the child goes to school and copes with a reduced academic pupil load. Computer tomography of the brain has revealed symptoms of a moderate diffuse atrophic process with the presence of two small-size cystic cavities in the subcortical portions of the right parietal lobe. Asymmetric broadening of the ventricular system, from the left greater than from the right. Magnetic resonance tomography of the cervical portion of the spine has not revealed compression of the spinal cord and its roots. The subarachnoidal space is completely passable, without symptoms of compression.

The patient was treated in accordance with the proposed method for neurosurgical treatment of ICP. Laminectomy was performed to provide access to the vertebral canal and its contents. The laminectomy was carried out in the cervical portion of the spine, and three chords of the second, third and fourth vertebrae were removed ($C_2$–$C_4$). The status of epiduritis was revealed, revision of the epidural space was carried out with accurate excision of the cicatrices and commissures formed from pathological epidural cellular tissue. One suture was placed on a single tear of the dura mater. In the postoperative period, 2 weeks after the operation, positive neurologic symptomatics began to appear in the form of progressing reduction of spasticity in the right extremities, an increase in the range of movements in them, normalization of the physiological rhythm of the pelvic organs, regress of hypesthesia (of abnormally diminished sensitiveness in the right extremities). When being discharged from the clinic, an improvement in the psychic functions and an increase in the intellectual abilities of the patient were noted.

So, checking the present invention under clinical conditions allows one to draw a conclusion that in the proposed method of neurosurgical treatment of infantile cerebral palsy, owing to performing broad laminectomy in a prescribed portion of the spine, elimination of hidden in obvious compression of the spinal cord roots and of the spinal cord itself and of the truncus cerebri is provided, whereby the existent status of spastic paresis or palsy of the upper and lower extremities, truncal disorders of the brain are eliminated, the psychic condition and intellectual abilities of patients are improved, the effectiveness of treatment being thus enhanced.

What is claimed is:

1. A method of neurosurgical treatment of infantile cerebral palsy, comprising the following sequential operations:
   performing laminectomy in the cervical portion of the spine for providing access to the vertebral canal and its contents; and
   removing at least three vertebral arches.

2. A method according to claim 1, wherein an additional examination is carried out before said laminectomy.

3. A method according to claim 2 wherein cranial dopplerography with investigating the cerebral blood flow rate and the Gosling pulse index along vertebral arteries, and computer thermal imaging investigation of the posterior surface of the neck are carried out during said additional examination.

4. A method of neurosurgical treatment according to claim 1 wherein at least one strip of a biological protector is placed on the dura mater to hermetize the membranes and stop liquorrhea.

5. A method according to claim 1, wherein, after removing the at least three vertebral arches, a spondylodesis implant of a biocompatible material is installed in the area of the laminectomy window.

* * * * *